(12) United States Patent
Barone et al.

(10) Patent No.: US 9,138,388 B2
(45) Date of Patent: Sep. 22, 2015

(54) SHINY, TRANSFER RESISTANT LIPSTICK AND METHOD OF MAKING

(75) Inventors: Salvatore J. Barone, Staten Island, NY (US); Lethu Nguyen, Colonia, NJ (US); Fredericke Vance Maillard, Paris (FR)

(73) Assignee: Coty Inc., New York, NY (US)

( * ) Notice: Subject to any disclaimer, the term of this patent is extended or adjusted under 35 U.S.C. 154(b) by 0 days.

(21) Appl. No.: 13/822,483

(22) PCT Filed: Nov. 8, 2011

(86) PCT No.: PCT/US2011/059710
§ 371 (c)(1),
(2), (4) Date: Jun. 26, 2013

(87) PCT Pub. No.: WO2012/064714
PCT Pub. Date: May 18, 2012

(65) Prior Publication Data
US 2013/0272982 A1    Oct. 17, 2013

Related U.S. Application Data

(60) Provisional application No. 61/411,170, filed on Nov. 8, 2010.

(51) Int. Cl.
| | |
|---|---|
| *A61K 8/31* | (2006.01) |
| *A61Q 5/00* | (2006.01) |
| *A61Q 1/06* | (2006.01) |
| *A61Q 3/02* | (2006.01) |
| *A61K 8/34* | (2006.01) |
| *A61K 8/37* | (2006.01) |
| *A61K 8/81* | (2006.01) |
| *A61K 8/92* | (2006.01) |

(52) U.S. Cl.
CPC . *A61K 8/31* (2013.01); *A61K 8/345* (2013.01); *A61K 8/375* (2013.01); *A61K 8/8111* (2013.01); *A61K 8/8117* (2013.01); *A61K 8/922* (2013.01); *A61Q 1/06* (2013.01); *A61Q 3/02* (2013.01); *A61Q 5/00* (2013.01); *A61K 2800/594* (2013.01)

(58) Field of Classification Search
CPC ............. A61K 8/31; A61Q 5/00; A61Q 1/06; A61Q 3/02
USPC .................. 424/61, 63, 64, 74, 757
See application file for complete search history.

(56) References Cited

U.S. PATENT DOCUMENTS

| | | | |
|---|---|---|---|
| 5,505,937 A | 4/1996 | Castrogiovanni et al. | |
| 6,033,650 A | 3/2000 | Calello et al. | |
| 6,036,947 A | 3/2000 | Barone et al. | |
| 6,143,283 A | 11/2000 | Calello et al. | |
| 6,682,748 B1 | 1/2004 | De La Poterie et al. | |
| 7,674,848 B2 | 3/2010 | Lin | |
| 2002/0018791 A1* | 2/2002 | Vatter et al. | 424/401 |
| 2003/0180338 A1* | 9/2003 | Arnaud et al. | 424/401 |
| 2007/0141003 A1* | 6/2007 | Blin et al. | 424/64 |
| 2008/0085961 A1* | 4/2008 | Lin | 524/313 |

FOREIGN PATENT DOCUMENTS

| | | | |
|---|---|---|---|
| CN | 1225260 A | 8/1999 | |
| CN | 103370050 A | 10/2013 | |
| WO | WO 2010/115973 A1 * | 10/2010 | A61K 8/92 |
| WO | WO-2010115973 | 10/2010 | |
| WO | WO-2012064714 | 5/2012 | |

OTHER PUBLICATIONS

Hydracire S—Jojoba Wax, Sunflower Wax & Mimosa Wax: retrieved from internet: alliance2u.com/pdf/Bulletin22.pdf. Retrieved on Sep. 6, 2013.*
Developments in Oleochemicals: retrieved from internet: www.neilaburns.com/wp.../08/Neil-Burns-Oleochem-Berlin-2009.pdf. Retrived on Sep. 6, 2013.*
"International Application Serial No. PCT/US2011/059740, International Preliminary Report on Patentability mailed May 23, 2013", 7 pgs.
"Chinese Application Serial No. 201180053855.5, Office Action mailed Apr. 17, 2014", 10 pgs.
"Chinese Application Serial No. 201180053855.5, Response filed Aug. 27, 2014 to Office Action mailed Apr. 17, 2014", (w/ English Translation of Amended Claims), 11 pgs.
"Chinese Application Serial No. 201180053855.5, Office Action mailed Dec. 15, 2014", 6 pgs.

* cited by examiner

*Primary Examiner* — Ernst V Arnold
*Assistant Examiner* — Hong Yu
(74) *Attorney, Agent, or Firm* — Schwegman Lundberg & Woessner, P.A.

(57) ABSTRACT

Inventive subject matter disclosed herein relates to method embodiments for imparting transfer resistance to a lipstick, comprising: Adding to one or more colorants, a coconut alkane mixture comprising a volatile oily composition having from 50 to 100% by weight of a mixture of linear paraffins that include 70 to 99% by weight of at least one linear paraffin selected from C(5), $C_{10}$, $C_{12}$ paraffins and mixtures thereof; heating A coconut gel comprising vegetable oil, Cocos Nucifera Oil, a styrene/butadiene copolymer and polyethylene; and adding the colorant and coconut alkane mixture and coconut gel together.

14 Claims, No Drawings

SHINY, TRANSFER RESISTANT LIPSTICK AND METHOD OF MAKING

CLAIM OF PRIORITY

This patent application is a U.S. National Stage Filing under 35 U.S.C. §371 of International Patent Application Serial No. PCT/US2011/059740, filed on Nov. 8, 2011, and published on May 18, 2012 as WO 2012/064714, which claims the benefit of priority of U.S. Provisional Patent Application Ser. No. 61/411,170, entitled SHINY, TRANSFER RESISTANT LIPSTICK AND METHOD OF MAKING, which was filed on Nov. 8, 2010, and which are hereby incorporated by reference herein in their entirety.

FIELD

Inventive subject matter disclosed herein relates to lipstick and other anhydrous cosmetic embodiments and method embodiments for making lipstick and other anhydrous cosmetics having shiny, transfer resistant properties.

BACKGROUND

Lip coloring has had a long and interesting history. Women started coloring their lips at least about 5000 years ago when Mesopotamian women decorated their lips with crushed jewels. About 1500 BC to 3000 BC, women in the Indus Valley colored their lips with a red dye. According to Meg Cohen Ragas and Karen Kozlowski in their book, "Read My Lips: A Cultural History of Lipstick," Egyptian women colored their lips with henna and with a preparation that included a purplish-red dye obtained from seaweed, iodine, and bromine marmite. It is believed that Cleopatra colored her lips with a formulation that included a dye extracted from crushed carmine beetles and ants.

During the period of Queen Elizabeth I, women colored their lips with a formulation that included beeswax and red dye. Queen Elizabeth herself, colored her lips black according to some sources and red, according to others. According to Ragas and Kozlowski, Thomas Hall, an English pastor and author of the "Loathsomeness of Long Haire" (1653), led a movement declaring that face painting was "the devil's work" and that women who put brush to mouth were trying to "ensnare others and to kindle a fire and flame of lust in the hearts of those who cast their eyes upon them." In 1770, the British Parliament passed a law condemning lipstick, stating that "women found guilty of seducing men into matrimony by a cosmetic means could be tried for witchcraft."

Modern lip coloring was formulated by perfumers in Paris in 1884. The lip coloring was wrapped in silk paper and made with deer tallow, castor oil and beeswax.

SUMMARY

Embodiments claimed and claimed herein include a lipstick comprising: a colorant paste comprising one or more dry pigments and coconut alkanes comprising a volatile oily composition having from 50 to 100% by weight of a mixture of linear paraffins that include 70 to 99% by weight of at least one linear paraffin selected from $C(5)$, $C_{10}$, $C_{12}$ paraffins and mixtures thereof; a coconut gel comprising vegetable oil, Cocos Nucifera Oil, a styrenelbutadiene copolymer and polyethylene; and polyethylene, caprylyl glycol, and a mixture of Acacia Decurrens/Jojoba/Sunflower Seed wax/Polyglyceryl 3-ester in concentrations effective for ensuring coconut alkanes are melted and homogeneous.

Embodiments also include a method for imparting transfer resistance to a lipstick, comprising: adding to one or more colorants, a coconut alkane mixture comprising a volatile oily composition having from 50 to 100% by weight of a mixture of linear paraffins that include 70 to 99% by weight of at least one linear paraffin selected from $C(5)$, $C_{10}$, $C_{12}$ paraffins and mixtures thereof; heating a coconut gel comprising vegetable oil, Cocos Nucifera Oil, a styrene/butadiene copolymer and polyethylene; and adding the colorant and coconut alkane mixture and coconut gel together.

Embodiments further include a method for making a lipstick having transfer resistance, comprising: combining one or more dry pigments with an amount of coconut alkanes comprising a volatile oily composition haying from 50 to 100% by weight of a mixture of linear paraffins that include 70 to 99% by weight of at least one linear paraffin selected from $C(5)$, $C_{10}$, $C_{12}$ paraffins and mixtures thereof effective to form a colorant paste; heating a mixture of a coconut gel comprising vegetable oil, Cocos Nucifera Oil, a styrene/butadiene copolymer and polyethylene to a temperature of about 85 to 90 degrees Centigrade; heating coconut alkanes comprising a volatile oily composition having from 50 to 100% by weight of a mixture of linear paraffins that include 70 to 99% by weight of at least one linear paraffin selected from $C(5)$, $C_{10}$, $C_{12}$ paraffins and mixtures thereof; adding the heated coconut gel to the heated coconut alkanes; adding the colorant paste to the mixture of coconut gel and coconut alkanes; and optionally adding fragrance and mica, ground pearl.

Inventive embodiments also include anhydrous cosmetic composition embodiments. The anhydrous cosmetic composition embodiments include coconut alkanes comprising a volatile oily composition having from 50 to 100% by weight of a mixture of linear paraffins that include 70 to 99% by weight of at least one linear paraffin selected from $C(5)$, $C_{10}$, $C_{12}$ paraffins and mixtures thereof. The composition also includes a coconut gel comprising vegetable oil, Cocos Nucifera Oil, a styrene/butadiene copolymer and polyethylene. The composition embodiments also include polyethylene, caprylyl glycol, and a mixture of Acacia Decurrens/Jojoba/Sunflower Seed wax/Polyglyceryl 3-ester in concentrations effective for ensuring coconut alkanes are melted and homogeneous; and one or more anhydrous actives.

DETAILED DESCRIPTION

The following detailed description includes references to embodiments, which are described in enough detail to enable those skilled in the art to practice the invention, The embodiments may be combined, other embodiments may be utilized, or structural, and logical changes may be made without departing from the scope of the present invention. The following detailed description is, therefore, not to be taken in a limiting sense, and the scope of the inventive subject matter is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation, Furthermore, all publications, patents, and patent documents referred to in this document are incorporated by reference herein in their entirety, as though individually incorporated by reference. in the event of inconsistent usages between this document and those documents so incorporated by reference, the usage in the incorporated reference should be considered supplementary to that of this document; for irreconcilable inconsistencies, the usage in this document controls.

Embodiments disclosed herein include a lipstick with long lasting transfer resistance. The lipstick embodiments include a gel having a vegetable oil, coconut oil and a styrenelbutadiene copolymer. One gel product that includes these ingredients is NatureVgel, manufactured by AppleChem, of Newark, N.J. The long lasting transfer resistance lipstick also includes coconut alkanes, provided in one embodiment, by a product called, Vegelight 1214C, manufactured by BioSyntheis, of St. Cyr Sous Dourdan, France. It is believed that the combination of the gel that includes vegetable oil, coconut oil, styrene/butadiene copolymer, and coconut alkanes imparts to the lipstick embodiments both long lasting transfer resistance and a long lasting shine. The lipstick embodiments described herein are manufactured in a stick form.

The term "stick" as used herein, refers to cosmetic compositions molded into the form of a stick. For some embodiments, the compositions are heated until molten and then poured into a mold and cooled. Stick embodiments also include anhydrous compositions capable of being formed into sticks.

One formulation embodiment of the shiny, long tasting transfer resistance is as follows

| # | INCI Name | Raw Material Name | % weight |
|---|---|---|---|
| Phase A | | | |
| 1 | Vegetable Oil, *Cocos Nucifera*(coconut)Oil and Styrene/Butadien Copolymer | NatureVgel-Fractionated coconut | 15.00 |
| 2 | Coconut Alkanes | Vegelight 1214 C | 41.12 |
| Phase B | | | |
| 3 | Polyethylene | Performalene 400 | 15.00 |
| Phase C | | | |
| 4 | *Acacia Decurrens/ Jojoba/Sunflower Seed wax/Polyglyceryl 3-ester* | Hydracire S | 5.00 |
| 5 | Caprylyl Glycol | Lexgard O | 0.50 |
| Phase D | | | |
| 6 | D&C Red#7 Calcium Lake | Red#7 C19-011 | 0.86 |
| 7 | IronOxides | Red Oxide C33-2199 | 1.90 |
| 8 | IronOxides | Black Oxide 300-401 | 0.79 |
| 9 | TITANIUM DIOXIDE | TiO2 C47-056 | 1.90 |
| 10 | Coconut Alkanes | Vegelight 1214C | 5.000 |
| Phase E | | | |
| 11 | Mica and Lauroyl Lysine | Mica with Lauroyl Lysine | 4.000 |
| 12 | TITANIUM DIOXIDE (and) MICA | TIMIRON MP-115 | 7.00 |
| 13 | MICA | Silk Mica | 1.53 |
| Phase F | | | |
| 14 | Fragrance | Fleuri | 0.40 |
| | TOTALS: | TOTALS: | 100.00 |

Ingredients of the shiny, long lasting transfer resistance include the following:

Gel

Gel embodiments include a blend of from 1 to 50 weight percent of at least one block copolymer, wherein the block copolymer has at least one polystyrene block and at least one unsaturated rubber block; and from 99 to 50 weight percent of natural oil. The composition results in a clear natural oil gel.

The block copolymer portion represents from 1 to 50% by weight of the composition. For some embodiments, the block copolymer is a single block copolymer or a mixture of different block copolymers. The block copolymers have unsaturated rubber blocks, for examples, SBS, SB, SIS, SI, (SB)n, and (SI)n. The block copolymers have a polystyrene content from 5% to 80%, for some embodiments from 10% to 50%, and for some embodiments, from 15% to 40% by weight of the block copolymer. Examples of these copolymers include Kraton® D Polymers and Vector® polymers.

The natural oils of the gel described herein may be plant or animal oils, and tend to be liquid at the room temperature. They are extracted from a wide range of plants and animals. An example of animal oils is fish oil. The most preferred natural oils of the invention are plant or vegetable oils. For example a preferred vegetable oil is jojoba oil, which is a monoester of eicosanoic and docosanoic acids and eicosanol and docosanol alcohols. Most other vegetable oils are triglycerides of glycerin and fatty acids which are largely unsaturated fatty acids such as oleic acid and linoleic acid. The vegetable oils of the present invention include non-genetically modified oils, genetically modified oils, organic grown oils, non-organic grown oils, and mixtures thereof.

In general, vegetable oils are readily available and prepared by extraction from plant seeds. Examples of the vegetable oils or plant oils include, but are not limited to, almond, avocado, castor, coconut, corn, cottonseed, olive, peanut, rice bran, safflower, sesame, soybean, sunflower, walnut, canola, refined palm, meadaowfoam, tea tree oil, etc.

The clear natural oil gels used in inventive lipstick embodiments described herein may additionally contain auxiliary ingredients including a) skirt compatible hydrophobic emollients including, but not limited to, sensory enhancers, synthetic esters, and hydrocarbon oils, the preferred ones being those derived from natural oils; b) skin benefit agents; and c) colorants, fumed silica, cornstarch, antioxidants, etc, Additional information regarding the gel is found in U.S. Pat. No 7,674,848, which is herein incorporated by reference.

Coconut Alkanes:

The coconut alkanes include a volatile oily composition having from 50 to 100% by weight of a mixture of linear paraffins that include 70 to 99% by weight of at least one linear paraffin selected from C(5), $C_{10}$, $C_{12}$ paraffins and mixtures thereof, (ii) 1 to 30% by weight of at least one $C_{14}$ to $C_{24}$ linear paraffin, and (b) from 0 to 50% by weight of at least one non-volatile oil.

As used herein, the word, "between" refers to including the cited limits.

The coconut alkanes have a volatility within the same range as cyclomethicones, i.e. a vapour pressure in the region of 0.001 to 300 mm Hg at ambient temperature (20° C.) and atmospheric pressure. The coconut alkanes form a film having a soft, non-greasy touch and a reduced gloss similar to those of cyclomethicones. This oily composition further has a flash point (measured as per the ASTM D93 standard) below 100° C., and/or a kinematic viscosity below 5 cSt, or between 1 and 3 cSt, at 40° C. This association of raw materials may thus partly or completely substitute the volatile silicones conventionally used in cosmetic compositions and more particularly cyclopentasiloxane and mixtures containing same (such as DC345® sold by DOW CORNING). The paraffins (or fatty alkanes) contained in the oily composition according to the invention may be advantageously obtained according to a method comprising the following successive steps:

1—dehydration of at least one $C_{14}$-$C_{24}$ fatty alcohol to obtain an alkene, and 2—hydrogenation of said alkene to an alkane. The first step of this method may particularly be implemented as described in the document US 2008/0287722, i.e. at a temperature of 190 to 260° C., for some embodiments, temperatures of 220 to 250° C., in the presence of a dehydration catalyst consisting of trifluoromethane sulphonic acid, which may represent 0.5 to 3% of the weight of the alcohol, for example. The alcohol dehydrated in this step may be obtained from plant sources and particularly be obtained by saponification of natural oils or fats. However, it is preferable for it to be obtained according to a method comprising a transesterification step of fatty acid triglycerides, for some embodiments, of plant origin, followed by a hydrogenation step of the fatty acid esters (for example methyl esters) obtained. The use of fatty alcohols of plant origin leads to alkenes containing an even number of carbon atoms, generally mixture form. This mixture may also comprise a minor amount of branched alkenes.

The second step of this method may be implemented in a conventional manner for those skilled in the art, according to techniques used in the food processing industry for hydrogenating oils, and particularly placing the alkene(s) in contact with a catalyst comprising a transition metal. The alkanes obtained preferably contain, as above, an even number of carbon atoms. They are linear, although they may also include a minor amount of branched alkanes.

Obviously, this method may further comprise other steps (preliminary, Intermediate and/or subsequent steps) than those mentioned above. Alternatively, commercially available paraffins, such as those available from SASOL under the brand name Parafol® (particularly Parafol® 14-97 for tetradecane) may be used in the oily composition according to the invention. The oily composition. according to the invention comprises 70 to 99% by weight, for example 70 to 90% or 90 to 99% by weight, $C_{10}$ and/or $C_{12}$ paraffin(s) and 1 to 30% by weight, for example 10 to 30% or 1 to 10% by weight, $C_{14}$ to $C_{24}$ paraffin(s). These two types of paraffins may be obtained separately and mixed, or obtained jointly from a mixture of fatty alcohols, particularly of plant origin, according to the method described above. Among the C(5), $C_{10}$ and/or $C_{12}$ paraffin(s), the $C_{12}$ paraffin is preferred. Moreover, as explained above, the $C_{14}$ to $C_{24}$ paraffin(s) are preferably chosen among those having an even number of carbon atoms, still preferably the $C_{14}$ paraffin. Furthermore, preferably, the oily composition according to the invention comprises, or consists only of, dodecane and tetradecane.

In addition to the abovementioned paraffins, and according to the desired. volatility, the oily composition according to the invention may contain at least one non-volatile oil. According to the present invention, the term "oil" refers to a liquid compound at ambient temperature (25° C.), which, when introduced at a rate of at least 1% by weight in water at 25° C., is not at all soluble in water, or soluble at a rate of less than 10% by weight, with reference to the weight of oil introduced into the water, In this description, the term "non-volatile oil" refers to an oil remaining on the skin at ambient temperature and atmospheric pressure for a plurality of hours, in the absence of friction, and/or having a vapour pressure less than 0.001 mm Hg under these conditions.

Examples of non-volatile oils include: mineral or synthetic branched hydrocarbons, synthetic (poly)esters and (poly) ethers and particularly (polyesters of $C_2$-$C_{24}$ (such as $C_6$-$C_{20}$) acids and $C_2$-$C_{24}$ (such as $C_6$-$C_{20}$) alcohols or polyols, which are advantageously branched, $C_o$-$C_{20}$ fatty acid triglycerides, vegetable oils, dialkyl carbonates such as dicaprylyl carbonate, branched and/or unsaturated fatty acids (such as linoleic and linolenic acids), branched and/or unsaturated fatty alcohols (such as octyldodecanol or hexyldecanol), silicone oils, fluorosilicone oils, fluorinated oils, and mixtures thereof. The term "hydrocarbon" refers to an oil containing only hydrogen and carbon atoms. Examples of non-volatile hydrocarbon oils are polybutene, hydrogenated polyisobutene, polydecene, hydrogenated polydecene, squalane, non-volatile paraffin oils and mixtures thereof. The (poly)esters of $C_2$-$C_{24}$ acids and $C_0$-$C_{20}$ alcohols and polyols, which represent the preferred category of non-volatile oils according to the invention, particularly include mono- and diesters such as ethyl acetate, isopropyl acetate, oleyl acetate, isononyl isononanoate, isononanoate, hexyl neopentanoate, ethylhexyl neopentanoate, isodecyl neopentanoate, isostearyl neopentanoate, heptyl undecylenate, neopentylglycol diheptanoate, neopentylglycol diethylhexanoate, pentaerythrityl tetraethylhexanoate, propanediol dicaprylate, neopentylglycol dicaprylate/dicaprate isopropyl myristate, isopropyl palmitate, hexyl laurate, the mixture of coco caprate and caprylate, $C_{12}$ to $C_{15}$ alcohol benzoates, and mixtures thereof.

Examples of vegetable oils are in particular wheat germ, sunflower, grape seed, sesame, corn, apricot, castor, shea, avocado, olive, soya, sweet almond, palm, rapeseed, cotton, hazelnut, macadamia, jojoba, alfalfa, poppy seed, pumpkin seed, sesame, marrow, rapeseed, blackcurrant, evening primrose, millet, barley, quinoa, rye, safflower, candlenut, passiflora, musk rose or camellia oils.

The term "silicone oil" refers to an oil comprising at least one silicon atom, and particularly at least one Si—O group. Non-volatile silicon oils particularly include polydimethylsiloxanes containing at least 8 silicon atoms, polyalkylmethylsiloxanes in which the alkyl chain contains 8 to 20 carbon atoms and oils identified using the INCI name phenyl trimethicone.

The oily composition according to the invention contains 50 to 100% by weight of paraffin mixture and 0 to 50% by weight of non-volatile oil(s), for example 70 to 95% by weight, for some embodiments, 85 to 95% by weight, of paraffin mixture and 5 to 30% by weight, for some embodiments, 5 to 15% by weight, of non-volatile oil(s). Oily compositions according to this invention are also marketed by One coconut alkane formulation is sold by BIOSYNTHIS under the trade name Vegelight® 1214.

The oily composition described above is advantageously intended for use in the formulation of a cosmetic, in particular, a lipstick.

Pigments and Powders

Lipstick embodiments also include one or more pigments and powders in a concentration range of 5-50% by weight of the total composition Particle size of the pigments and powders range from 0.02 to 200 microns. Suitable powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The powders described herein may be surface treated with lecithin, amino acids, mineral oil, silicone oil or various other agents either alone or in combination, which coat the powder surface and render the particles more lipophilic in nature.

Some powder embodiments include organic and inorganic pigments. The organic pigments include azo, indigoid, triphenylmethane, anthraquinone, and xanthine dyes which are designated as D &C and FD &C blues, browns, greens, oranges, reds, yellows, etc. Organic pigments include insoluble metallic salts of certified color additives, referred to as the Lakes. Inorganic pigments include iron oxides, ultramarines, chromium, chromium hydroxide colors, and mixtures thereof. Some composition embodiments include both pigment and non-pigmented powders. The weight ratio of pigment to non-pigmented powder will range from 1:20 to 20:1.

Fragrances

Embodiments disclosed herein are either fragrance free or include a fragrance compatible with lipstick, In one embodiment, the fragrance is Fleuri.

In one embodiment, the lipstick of high transfer resistance is made with a three-roller mill, a stirrer and a propeller. One step of the method includes preparing a colorant phase. The colorant phase includes combining colorant ingredients such as D&C Red NO. 7 Calcium Lake, iron oxides, titanium dioxide, and other colorants as desired. Coconut alkanes, such as Vegelight 1214C, are added to the colorant ingredients in a concentration effective to make a paste. The paste is passed through a 3-roller at least 3-4 times. The pigment grind is checked under a Hegman gauge to ensure good pigment dispersion.

In another step, a coconut gel, such as Nature Vgel, is added to a container, such as a reactor. The coconut gel is heated to 85 to 90° C. The coconut gel is mixed to obtain a uniform mixture. Polyethylene is added to the heated coconut gel at a temperature of 85 to 90° C. to form a PE-gel mixture. The PE-gel mixture is then well mixed to ensure that waxes are completely melted or homogeneous, Coconut alkanes, for some embodiments, Vegelight 1214C are added to the coconut gel and polyethylene mixture at a temperature of 85° C. to 90° C., forming a PE-gel-alkane mixture. The PE-gel-alkane mixture then mixed, Acacia Decurrens/Jojoba/Sunflower Seed wax/Polyglyceryl 3-ester is added to the PE-gel-alkane mixture. Caprylyl glycol is also added to the coconut alkanes, gel mixture.

The colorant paste, including the coconut alkanes, is quickly added to the heated mixture of coconut gel and polyethylene to form a new mixture. The new mixture is mixed and held at a temperature within a range of 85 to 90° C.

The temperature of 85° C. to 90° C. is maintained. Mica and lauroyl lysine, titanium dioxide and mica and mica are added one at a time to the new mixture.

For some embodiments, a fragrance is added to the mixture and mixed. The mixture is then poured into stick molds at 85° C., to make lipstick.

Compositions that include coconut alkanes having a volatile oily composition having from 50 to 100% by weight of a mixture of linear paraffins that include 70 to 99% by weight of at least one linear paraffin selected from C(5), $C_{10}$, $C_{12}$ paraffins and mixtures thereof; a coconut gel comprising vegetable oil, Cocos Nucifera Oil, a styrenelbutadiene copolymer and polyethylene; polyethylene, caprylyl glycol, and a mixture of Acacia Decurrens/Jojoba/Sunflower Seed wax/Polyglyceryl 3-ester in concentrations effective for ensuring coconut alkanes are melted and homogeneous; and one or more anhydrous actives are usable in a variety of anhydrous cosmetics, in addition to lipstick. The anhydrous cosmetics include skin care compositions, scalp care compositions, and compositions for hair, eyelashes and nails. The anhydrous cosmetics disclosed herein have an improved transfer resistance.

Skin care and other cosmetic anhydrous actives include but are not limited to petroleum-based emollients, vegetable oils, hydrogenated vegetable oils, and their derivatives; branched hydrocarbons; fatty alcohol ethers; free sterols, sterol esters and their derivatives; sphingolipids; phospholipids; and mixtures thereof. Suitable petroleum-based emollient include petrolatums, i.e., hydrocarbons or mixtures of hydrocarbons; particularly preferred are hydrocarbons having chain lengths of from C10 to C100. Petroleum-based emollients within this chain length range include mineral oil and petrolatum. Mineral oil usually refers to less viscous mixtures of hydrocarbons having from 10 to 30 carbon atoms, though the hydrocarbon molecular weight distribution may vary. Since the lower molecular weight hydrocarbons can cause irritation in some individuals, mineral oils having a small percentage of lower molecular weight hydrocarbons are preferred. Petrolatum usually refers to more viscous mixtures of hydrocarbons of higher molecular weight hydrocarbons.

The transfer resistance of a lipstick made with the formulation disclosed in the table herein was evaluated. In particular, panelists were given a blinded lipstick sample and applied an even coat of the lipstick and let it dry for fifteen minutes. All panelists were women above the age of eighteen years. Each panelist was given a white tile to kiss using moderate pressure. Three expert evaluators scored the amount of transfer according to the Lipstick Transfer Scale, as illustrated in FIG. 1.

No adverse reactions were reported. Expert evaluator scores are shown in the table below. To be considered a transfer-resistant lipstick, a lipstick must have an average score of 1.36.

| Evaluator 1 | Evaluator 2 | Evaluator 3 | Average | Panelist |
|---|---|---|---|---|
| 1 | 1 | 1 | 1 | 1.00 |
| 2 | 2 | 3 | 2.5 | 2.50 |
| 3 | 1 | 2.5 | 1.5 | 1.67 |
| 4 | 1 | 1 | 1 | 1 |
| 5 | 1.5 | 2 | 1.5 | 1.67 |
| 7 | 1 | 1 | 1 | 1.00 |
| 8 | 0.5 | 1 | 0.5 | 0.67 |

Mean 1.36

The embodiments are described in sufficient detail to enable those skilled in the art to practice the invention. Other embodiments may be utilized and formulation and method of using changes may be made without departing from the scope of the invention. The detailed description is not to be taken in a limiting sense, and the scope of the invention is defined only by the appended claims, along with the hill scope of equivalents to which such claims are entitled.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description

What is claimed is:
1. A lipstick comprising:
   a colorant paste comprising one or more dry pigments and coconut alkanes comprising a volatile oily composition having from 50 to 100% by weight of a mixture of linear paraffins that include 70 to 99% by weight of at least one linear paraffin selected from $C_5$, $C_{10}$, $C_{12}$ paraffins and mixtures thereof;

a coconut gel comprising vegetable oil, Cocos Nucifera Oil, a styrene/butadiene copolymer and polyethylene; and polyethylene, caprylyl glycol, and a mixture of Acacia Decurrens/Jojoba/Sunflower Seed wax/Polyglyceryl 3-ester in concentrations effective for ensuring coconut alkanes are melted and homogeneous wherein the lipstick displays transfer resistance and shine.

2. The lipstick of claim 1, further comprising lauroyl lysine, mica and pearls.

3. The lipstick of claim 1, further comprising fragrance.

4. A method for imparting transfer resistance to a lipstick, comprising:
  adding to one or more colorants, a coconut alkane mixture comprising a volatile oily composition having from 50 to 100% by weight of a mixture of linear paraffins that include 70 to 99% by weight of at least one linear paraffin selected from $C_5$, $C_{10}$, $C_{12}$ paraffins and mixtures thereof;
  heating a coconut gel comprising vegetable oil, Cocos Nucifera Oil, a styrene/butadiene copolymer and polyethylene;
  adding the colorant and coconut alkane mixture and coconut gel together; and
  adding polyethylene, caprylyl glycol, and a mixture of Acacia Decurrens/Jojoba/Sunflower Seed wax/Polyglyceryl 3-ester in concentrations effective for ensuring coconut alkanes are melted and homogeneous to the mixture of coconut alkanes and coconut gel.

5. The method of claim 4, wherein the coconut gel is heated to a temperature within a range of 85 degrees C. to 90 degrees C.

6. The method of claim 4, further comprising adding the final mixture to a mold at a temperature of 85 degrees C.

7. A method for making a lipstick having transfer resistance, comprising:
  combining one or more dry pigments with an amount of coconut alkanes comprising a volatile oily composition having from 50 to 100% by weight of a mixture of linear paraffins that include 70 to 99% by weight of at least one linear paraffin selected from $C_5$, $C_{10}$, $C_{12}$ paraffins and mixtures thereof effective to form a colorant paste;
  heating a mixture of a coconut gel comprising vegetable oil, Cocos Nucifera Oil, a styrene/butadiene copolymer and polyethylene to a temperature of about 85 to 90 degrees Centigrade;
  heating coconut alkanes comprising a volatile oily composition having from 50 to 100% by weight of a mixture of linear paraffins that include 70 to 99% by weight of at least one linear paraffin selected from C%, $C_{10}$, $C_{12}$ paraffins and mixtures thereof;
  adding the heated coconut gel to the heated coconut alkanes;
  adding polyethylene, caprylyl glycol, and a mixture of Acacia Decurrens/Jojoba/Sunflower Seed wax/Polyglyceryl 3-ester in concentrations effective for ensuring coconut alkanes are melted and homogeneous to the mixture of coconut gel and coconut alkanes; and
  optionally adding fragrance and mica, ground pearl.

8. The method of claim 5, wherein the heated mixture of coconut gel and heated coconut alkanes are poured into a stick mold to make a lipstick.

9. A lipstick comprising vegetable oil, cocos nucifera, coconut, oil and styrene/butadiene copolymer and coconut alkanes.

10. An anhydrous cosmetic comprising:
  Coconut alkanes comprising a volatile oily composition having from 50 to 100% by weight of a mixture of linear paraffins that include 70 to 99% by weight of at least one linear paraffin selected from $C_5$, $C_{10}$, $C_{12}$ paraffins and mixtures thereof;
  a coconut gel comprising vegetable oil, Cocos Nucifera Oil, a styrene/butadiene copolymer and polyethylene;
  polyethylene, caprylyl glycol, and a mixture of Acacia Decurrens/Jojoba/Sunflower Seed wax/Polyglyceryl 3-ester in concentrations effective for ensuring coconut alkanes are melted and homogeneous; and
  one or more anhydrous actives.

11. The anhydrous cosmetic of claim 10, wherein the one or more actives comprise a colorant paste.

12. The anhydrous cosmetic of claim 10, wherein the anhydrous cosmetic is a skin care composition.

13. The anhydrous cosmetic of claim 10, wherein the anhydrous cosmetic is a scalp care composition.

14. The anhydrous cosmetic of claim 10, wherein the anhydrous cosmetic is employed in compositions for one or more of hair, eyelashes and nails.

* * * * *

UNITED STATES PATENT AND TRADEMARK OFFICE
CERTIFICATE OF CORRECTION

PATENT NO. : 9,138,388 B2
APPLICATION NO. : 13/822483
DATED : September 22, 2015
INVENTOR(S) : Barone et al.

Page 1 of 1

It is certified that error appears in the above-identified patent and that said Letters Patent is hereby corrected as shown below:

On the Title Page, in item (86), in "PCT No.", in column 1, line 1, delete "PCT/US2011/059710" and insert --PCT/US2011/059740--, therefor Signed and Sealed this
Twenty-second Day of March, 2016

Michelle K. Lee
*Director of the United States Patent and Trademark Office*